(12) United States Patent
Svitek et al.

(10) Patent No.: US 9,532,898 B2
(45) Date of Patent: Jan. 3, 2017

(54) APPARATUS AND METHOD FOR RAPIDLY COOLING OR HEATING THE BODY TEMPERATURE OF A PATIENT

(75) Inventors: Robert G. Svitek, Freeport, PA (US); Kraig J. McEwen, Mars, PA (US); Rebecca L. Baptiste, Fairhaven, MA (US)

(73) Assignee: CardiacAssist, Inc., Pittsburgh, PA (US)

( * ) Notice: Subject to any disclaimer, the term of this patent is extended or adjusted under 35 U.S.C. 154(b) by 244 days.

(21) Appl. No.: 14/232,643

(22) PCT Filed: Jul. 16, 2012
(Under 37 CFR 1.47)

(86) PCT No.: PCT/US2012/046853
§ 371 (c)(1),
(2), (4) Date: Sep. 3, 2014

(87) PCT Pub. No.: WO2013/012776
PCT Pub. Date: Jan. 24, 2013

(65) Prior Publication Data
US 2015/0150715 A1    Jun. 4, 2015

Related U.S. Application Data

(60) Provisional application No. 61/508,257, filed on Jul. 15, 2011.

(51) Int. Cl.
*A61M 37/00* (2006.01)
*A61F 7/00* (2006.01)
(Continued)

(52) U.S. Cl.
CPC ............. *A61F 7/0085* (2013.01); *A61F 7/007* (2013.01); *A61M 1/14* (2013.01); *A61M 1/369* (2013.01);
(Continued)

(58) Field of Classification Search
CPC .. A61M 1/369; A61M 1/14; A61M 2205/366; A61F 2007/0069; A61F 2007/0076; A61F 2007/126; A61F 7/007; A61F 7/0085
(Continued)

(56) References Cited

U.S. PATENT DOCUMENTS

| 4,047,563 A | 9/1977 | Kurata |
| 4,177,816 A | 12/1979 | Torgeson |

(Continued)

FOREIGN PATENT DOCUMENTS

| WO | 9511709 A2 | 5/1995 |
| WO | 2004101021 A2 | 11/2004 |

(Continued)

*Primary Examiner* — Leslie Deak
(74) *Attorney, Agent, or Firm* — The Webb Law Firm

(57) ABSTRACT

An extracorporeal blood cooling or heating circuit includes an intravenous catheter for withdrawing a patients blood coupled to a combined pump/heat exchanger device. One or more sensors are provided upstream and/or downstream of the pump/heat exchanger device for measuring pressure, temperature, fluid flow, blood oxygenation, and other parameters. A controller is operatively coupled to the pump/heat exchanger device and the one or more sensors to control the speed of the pump inside the pump/heat exchanger device and regulate the blood temperature by controlling the operation of the heat exchanger. The combined pump/heat exchanger device includes a housing having at least one inlet and at least one outlet, a pump portion defining a blood circuit inside the housing, and a heat exchanger portion contained within the housing for selectively heating or cooling the blood.

16 Claims, 5 Drawing Sheets

(51) Int. Cl.
    *A61M 1/36*     (2006.01)
    *F28D 7/16*     (2006.01)
    *A61M 1/14*     (2006.01)
    *F28D 21/00*     (2006.01)
    *A61F 7/12*     (2006.01)

(52) U.S. Cl.
    CPC .......... *A61M 1/3609* (2014.02); *F28D 7/1615* (2013.01); *F28D 7/1669* (2013.01); *A61F 2007/0069* (2013.01); *A61F 2007/0076* (2013.01); *A61F 2007/126* (2013.01); *A61M 2205/366* (2013.01); *A61M 2205/3673* (2013.01); *F28D 2021/005* (2013.01); *F28F 2250/08* (2013.01)

(58) Field of Classification Search
    USPC ........................................................ 604/6.13
    See application file for complete search history.

(56) References Cited

U.S. PATENT DOCUMENTS

| | | | |
|---|---|---|---|
| 4,902,476 A * | 2/1990 | Gordon | A61M 1/1698 128/DIG. 3 |
| 5,514,335 A | 5/1996 | Leonard et al. | |
| 6,413,233 B1 | 7/2002 | Sites et al. | |
| 6,626,857 B1 * | 9/2003 | Ohta | A61M 1/369 422/44 |
| 6,827,898 B1 | 12/2004 | Fausset et al. | |
| 7,022,284 B2 * | 4/2006 | Brian | A61M 1/1698 128/DIG. 3 |
| 7,473,395 B2 | 1/2009 | Zviman et al. | |
| 7,588,549 B2 | 9/2009 | Eccleston | |
| 2004/0223872 A1 | 11/2004 | Brian et al. | |
| 2005/0027281 A1 * | 2/2005 | Lennox | A61F 7/12 604/508 |
| 2006/0173396 A1 | 8/2006 | Hatamian et al. | |
| 2006/0293732 A1 | 12/2006 | Collins et al. | |
| 2007/0253463 A1 | 11/2007 | Perry et al. | |
| 2008/0146995 A1 | 6/2008 | Smisson et al. | |
| 2008/0234623 A1 | 9/2008 | Strauss et al. | |
| 2010/0243208 A1 * | 9/2010 | Kar | B01J 8/067 165/96 |
| 2012/0029408 A1 | 2/2012 | Beaudin | |

FOREIGN PATENT DOCUMENTS

| | | |
|---|---|---|
| WO | 2006063080 A1 | 6/2006 |
| WO | 2007120812 A2 | 10/2007 |
| WO | 2010107881 A1 | 9/2010 |
| WO | 2010111778 A1 | 10/2010 |

* cited by examiner

APPARATUS AND METHOD FOR RAPIDLY COOLING OR HEATING THE BODY TEMPERATURE OF A PATIENT

BACKGROUND OF THE INVENTION

Field of the Invention

This invention relates, in general, to blood perfusion systems, and more particularly, to an apparatus and a method for rapidly cooling or heating the body temperature of a patient.

Description of the Related Art

Patients who experience severe medical trauma, such as a stroke, heart attack, or cardiac arrest, can benefit from cooling the body to below normal body temperature shortly after experiencing the trauma. Studies have shown that the medical outcome for such patients is significantly improved if they are treated within 90 minutes of arriving to the hospital. During surgery, the patient's body is typically cooled to induce hypothermia in order to protect the organs. In certain medical situations, such as post-surgery, it is desirable to reheat the patient's blood to a normal body temperature. The measure of damage to the cardiac muscle in patients who have had an acute myocardial infarction is directly correlative to the infarcted area. Studies have shown that rapid increases or decreases of the patient's body temperature reduce the infarct size and improve recovery outcome. Similar results have been shown in stroke patients for preserving neurological function and contrast-injected patients to preserve kidney function.

Existing systems and methods for reducing the temperature of a patient include infusion of cold saline through endovascular cooling catheters having separate lumens for saline flow and blood flow. Other systems and methods rely on heating or cooling pads which are applied directly to the patient's body. Cardiopulmonary bypass is a typical method of cooling the patient's heart, while several similar bypass methods are known to cool the patient's brain. These existing systems and methods are often cumbersome and do not reduce the temperature of the patient's body quickly enough to have a beneficial medical outcome. Additionally, existing systems are often only capable of either heating or cooling the patient's body, therefore requiring multiple devices present within an operating room.

Known systems based on extracorporeal blood extraction circuits typically have conduits carrying blood from the patient through heat exchangers in order to perform controlled heating or cooling of the blood. Conduits typically include endovascular catheters inserted into the patient's vascular system. Heat exchangers for cooling the patient's body often include an ice bath for cooling the endovascular catheter directly or cooling the water or saline solution that is passed through a conduit in the catheter. Similarly, heat exchangers for heating the patient's body typically include one or more heating devices for heating the endovascular catheter directly or heating the water or saline solution that is passed through the catheter lumen. In certain devices, a controller may be coupled to a plurality of sensors to regulate the heat exchanger and/or the pump.

Within the prior art, U.S. Pat. No. 7,473,395 to Zviman et al. teaches a hypothermia induction device for recirculating blood through an extracorporeal circuit using a single venous access. The device includes a withdrawal pump, an infusion pump, a chiller and heat exchanger, and optional modules for further blood treatment. A controller adjusts the operation of withdrawal and infusion pumps based on pressures sensed in catheter lines between the patient and the device. This system is only capable of cooling the blood by maximizing the withdrawal rate to maintain a predetermined temperature.

U.S. Pat. No. 7,588,549 to Eccleston is directed to a thermoelectric temperature control device for an extracorporeal blood circuit. The device includes a heat exchanger cassette having a central core and two flow guides in thermal contact with a thermoelectric module. A plurality of parallel channels pass through the cassette to guide blood to and from the device in a substantially laminar flow. A controller regulates the voltage and current of the thermoelectric module to control the temperature differential produced by the device.

United States Patent Application Publication No. 2006/0293732 to Collins et al. discloses a thermoelectric cooler and heat exchanger for an intravascular heat exchange catheter. The system incorporates a secondary heat exchange element in thermal contact with a thermoelectric cooler assembly. Heat is removed from the thermoelectric cooler assembly via a reservoir connected to a circulating fluid supply. A controller regulates the power level supplied to the thermoelectric cooler assembly. Optionally, the controller may also regulate the fluid flow to and from the reservoir.

Numerous disadvantages are associated with the existing devices for heating or cooling the body temperature of a patient. In most known systems, the heater and/or cooler is contained within a separate unit from the pump. This arrangement is bulky in size and therefore requires additional space within the operating room. Additionally, most known systems are capable of either heating or cooling the blood, which requires hospitals to get separate units for both heating and cooling. This duplication not only adds additional expense, but also further reduces the available space in already cramped operating rooms. Furthermore, large pump priming volume is required due to the separation of the pump from the heat exchange element. Many known systems are inefficient at adding heat to and/or removing heat from the patient's blood and therefore require large heat exchangers having a large volume of blood present within them.

SUMMARY OF THE INVENTION

In view of the foregoing, a need exists for an apparatus and method for rapidly cooling or heating the body temperature of a patient using an efficient pump/heat exchanger system. It is desirable to provide a system having heat exchange capacity in order to rapidly heat or cool the patient's blood. An additional need exists for reducing the pump priming volume. A further need exists for a compact system that is easily integrated within an operating room.

According to one embodiment, an apparatus for rapidly cooling or heating the body temperature of a patient includes a housing having at least one inlet and at least one outlet, a pump portion contained within the housing for extracting blood from and infusing blood to a patient's body, the pump portion defining a blood circuit inside the housing being fluidly connected with at least one fluid inlet and at least one fluid outlet, and a heat exchanger portion contained within the housing for selectively heating or cooling the blood. The heat exchanger portion may be fluidly connected with at least one fluid inlet to receive a heat exchange fluid and at least one fluid outlet to expel the heat exchange fluid, the fluid inlet and the fluid outlet defining a fluid circuit therebetween. Alternatively, the heat exchanger portion may include a Peltier device having one or more thermoelectric modules in thermal contact with a blood conduit.

According to another embodiment, a first inlet may be a blood inlet to receive the blood into the housing and a first outlet may be a blood outlet for expelling the blood from the housing. The blood inlet and the blood outlet may be fluidly connected inside the housing via the blood circuit. Similarly, a second fluid inlet may be a fluid inlet to receive the heat exchange fluid into the housing, and a second outlet may be a fluid outlet for expelling the heat exchange fluid from the housing. The fluid inlet and the fluid outlet may be fluidly connected inside the housing via the fluid circuit such that the blood circuit and the fluid circuit are in fluid isolation from each other inside the housing.

In accordance with another embodiment, the heat exchanger portion may further include a plurality of heat exchange tubes operative for flowing the heat exchange fluid therethrough. The plurality of heat exchange tubes may be in thermal contact with the blood circuit. The blood circuit may include a first chamber for receiving the blood from the blood inlet, a blood conduit for delivering the blood from the first chamber into a pump, and a second chamber for receiving the blood from the pump. The second chamber may be within the heat exchanger portion of the housing such that blood within the second chamber is in thermal contact with the heat exchanger portion. Desirably, the apparatus may be made from a material having high thermal conductivity to facilitate heat transfer between the blood inside the blood circuit and the heat exchange fluid inside the fluid circuit.

According to another embodiment, an extracorporeal blood cooling or heating circuit may include a catheter for withdrawing blood from a patient into the extracorporeal blood cooling or heating circuit and infusing blood into the patient from the extracorporeal blood cooling or heating circuit and a combined pump/heat exchanger device for selectively cooling or heating the blood. One or more sensors operative for measuring blood temperature, pressure, flow, or oxygenation may also be provided. Additionally, a controller may be provided such that the controller is operatively connected to the combined pump/heat exchanger and one or more sensors for controlling the operation of extracorporeal blood cooling or heating circuit and selectively cooling or heating the blood. The circuit may further include one or more modules operative for treating the blood. The one or more modules may be a blood oxygenation device or a hemodialysis device.

According to yet another embodiment, a method for rapidly cooling or heating the body temperature of a patient may include the steps of withdrawing blood from a patient into an extracorporeal circuit having a combined pump/heat exchanger having a pump portion and a heat exchanger portion, selectively cooling or heating the blood within the heat exchanger portion to a desired temperature, and returning the blood to the patient. The combined pump/heat exchanger device may include a housing having at least one inlet and at least one outlet, a pump portion contained within the housing for extracting blood from and infusing blood to a patient's body, the pump portion defining a blood circuit inside the housing being fluidly connected with at least one fluid inlet and at least one fluid outlet, and a heat exchanger portion contained within the housing for selectively heating or cooling the blood. The heat exchanger portion may be fluidly connected with at least one fluid inlet to receive a heat exchange fluid and at least one fluid outlet to expel the heat exchange fluid, the fluid inlet and the fluid outlet defining a fluid circuit therebetween.

Further details and advantages of the various embodiments set forth in this disclosure will become clear from the following detailed description read in conjunction with the drawings.

DETAILED DESCRIPTION OF THE INVENTION

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered limiting.

Figure 1:
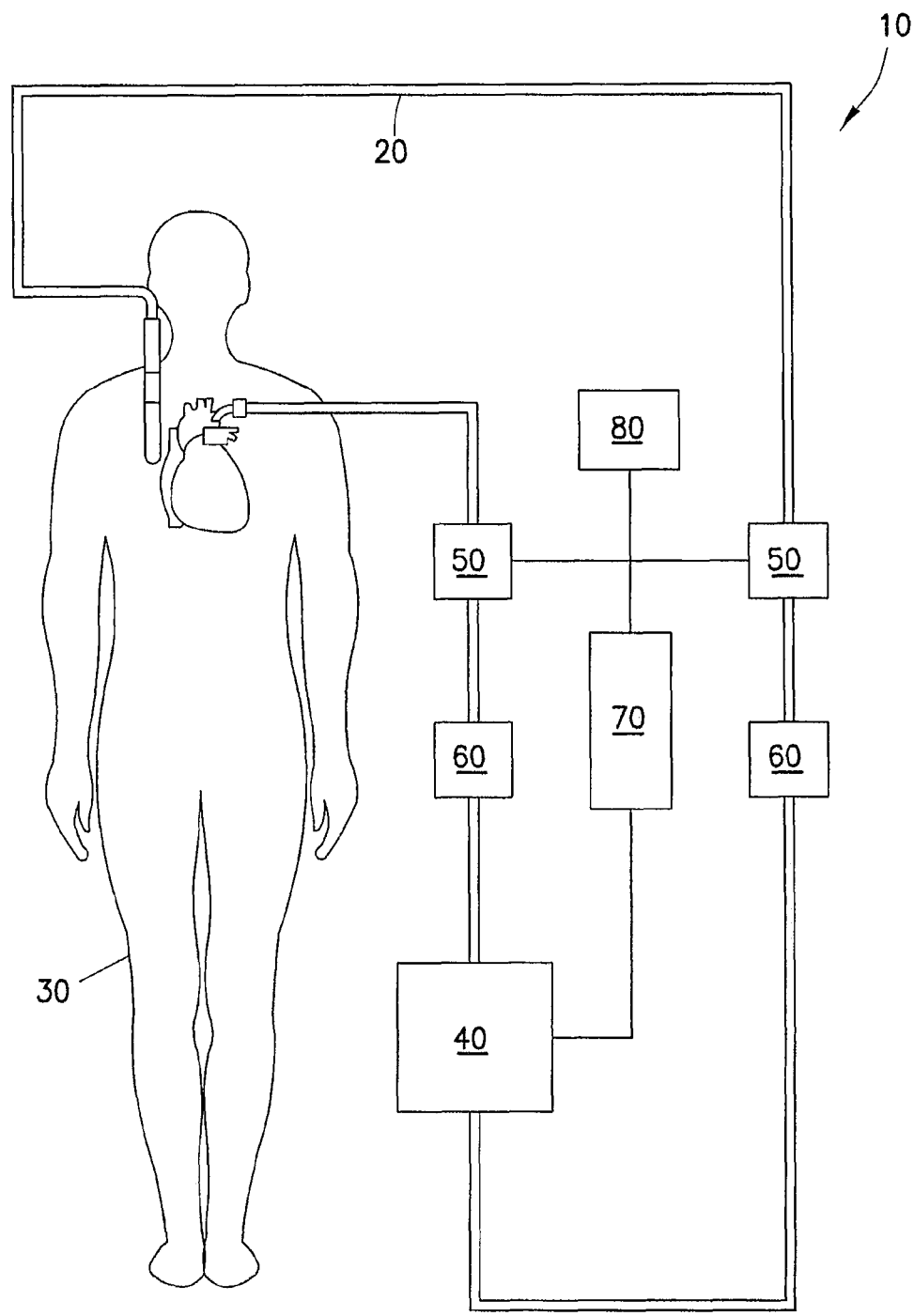
FIG. 1 is a schematic diagram of one embodiment of an extracorporeal blood cooling or heating circuit.

Referring to the drawings in which like reference characters refer to like parts throughout the several views thereof, several embodiments of an apparatus and method for rapidly cooling or heating the body temperature of a patient are presented. With reference to FIG. 1, an extracorporeal blood cooling or heating circuit 10 in accordance with one embodiment is shown. The extracorporeal blood cooling or heating circuit 10 includes an intravenous catheter 20 inserted into a patient 30 for withdrawing the patient's blood into the extracorporeal blood cooling or heating circuit 10. The catheter 20 is desirably inserted to a suitable point inside patient's vascular system to unload the patient's heart during extracorporeal blood cooling or heating and return the blood to the patient after it has been heated or cooled. Catheter 20 may be, for example, a central venous catheter placed into a patient's neck (internal jugular vein or external jugular vein), chest (subclavian vein), or groin (femoral vein). In some embodiments, catheter 20 may be inserted, for example, into the left atrium of the patient's heart to withdraw blood into the circuit 10. Optionally, catheter 20 may have a dual-lumen design, such that catheter 20 may be placed into a vessel to withdraw blood and return it to a nearby location, desirably downstream, after the blood has been heated or cooled. In other embodiments, two independent catheters may be used, wherein one catheter is used for blood withdrawal and the other catheter is used for blood return.

With continuing reference to FIG. 1, the catheter 20 is coupled to a combined pump/heat exchanger device 40 which can selectively cool or heat the patient's blood. One or more sensors 50 may be provided upstream and/or downstream of the pump/heat exchanger device 40. The one or more sensors 50 are operative for measuring, for example, pressure, temperature, fluid flow, blood oxygenation, and other essential parameters. The circuit 10 may further include one or more modules 60 for optional blood treatment. The one or more modules 60 may be provided upstream or downstream of the pump/heat exchanger device 40, or they may be combined therewith. Additionally, the one or more modules 60 may contain one or more sensors 50. The one or more modules 60 may be operative for blood oxygenation or dialysis. For example, module 60 may be a blood oxygenator to regulate the oxygen content in the patient's blood.

The extracorporeal blood cooling or heating circuit 10 further includes a controller 70 operatively coupled to the pump/heat exchanger device 40, one or more sensors 50, and/or one or more modules 60. The controller 70 receives power from a power supply (not shown) and controls the operation of the circuit 10. For instance, the controller 70 controls the speed of the pump inside the pump/heat exchanger device 40 to regulate the blood withdrawal rate. Additionally, the controller 70 monitors blood temperature provided by the one or more sensors 50 and controls the operation of the heat exchanger in response to the temperature values. In some embodiments, the controller 70 may be provided with an interface 80 to provide an indication of the operating status of the circuit 10. The controller 70 may further regulate the operation of the one or more modules 60 for further blood processing.

Figure 2:
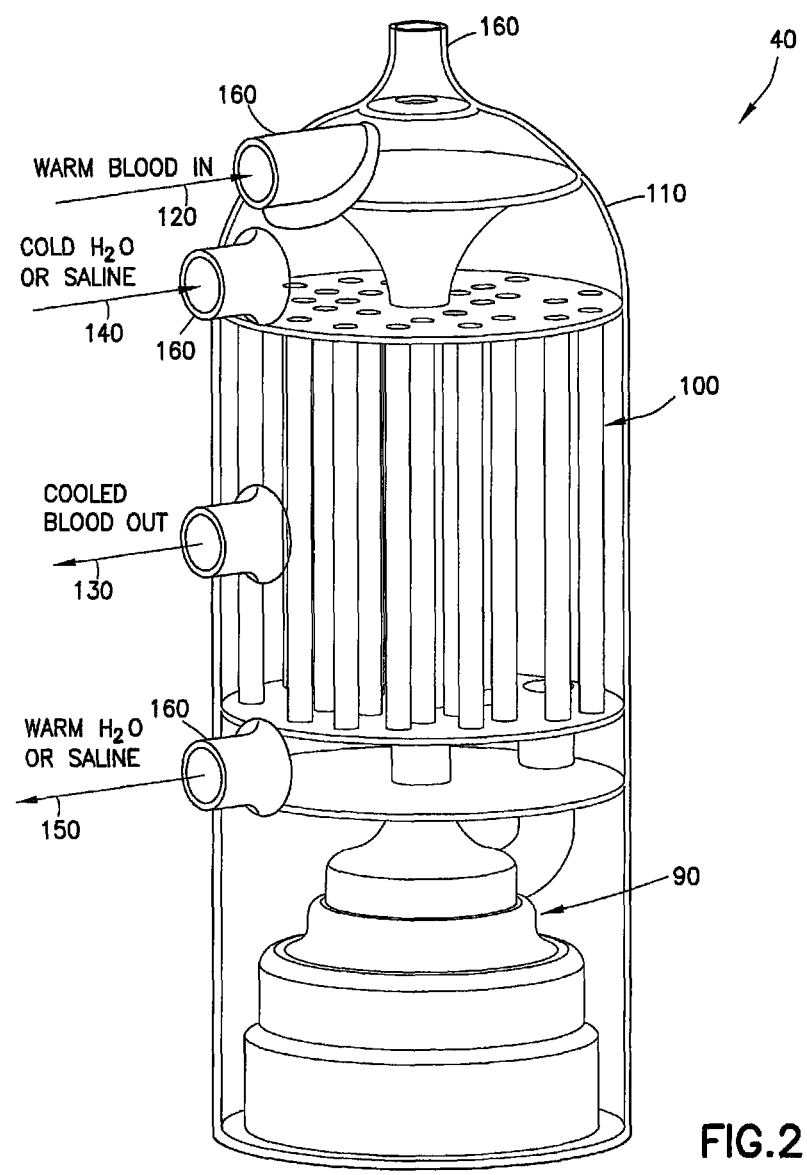
FIG. 2 is perspective view of a combined pump/heat exchanger according to one embodiment.

With reference to FIG. 2, venous blood is withdrawn by a pump 90 of a combined pump/heat exchanger device 40. As will be described herein, the pump 90 may be a conventional arterial blood pump, including, for example, a centrifugal pump or a roller pump. The pump 90 may be mechanically driven or powered by an electric motor. In some embodiments, the pump 90 has an electromagnetic drive. The pump 90 is directly integrated with a heat exchanger 100 such that the pump 90 and the heat exchanger 100 share a common housing 110. Housing 110 is shown in FIG. 2 as having a generally cylindrical shape, however other housing shapes may be used and the cylindrical shape is for exemplary purposes.

With continuing reference to FIG. 2, the combined pump/heat exchanger device 40 includes a plurality of fluid inlet ports and fluid outlet ports disposed on the housing 110. A blood inlet 120 is provided for receiving blood from the patient 30 into the pump/heat exchanger device 40. Similarly, a blood outlet 130 expels the blood once it passes through the pump/heat exchanger device 40. A fluid inlet 140 receives heat exchange fluid coining into the pump/heat exchanger device 40, while a fluid outlet 150 expels the heat exchange fluid after it passes through the pump/heat exchanger device 40. Fittings 160 may be provided on each of the fluid inlet ports and fluid outlet ports 140, 150 for attaching conventional devices for carrying perfused blood, such as the catheter 20. The fittings 160 may include a barbed connection, or an otherwise known connection arrangement used in the medical field, to facilitate the coupling of tubing to the housing 110 of the pump/heat exchanger device 40.

Figure 3:
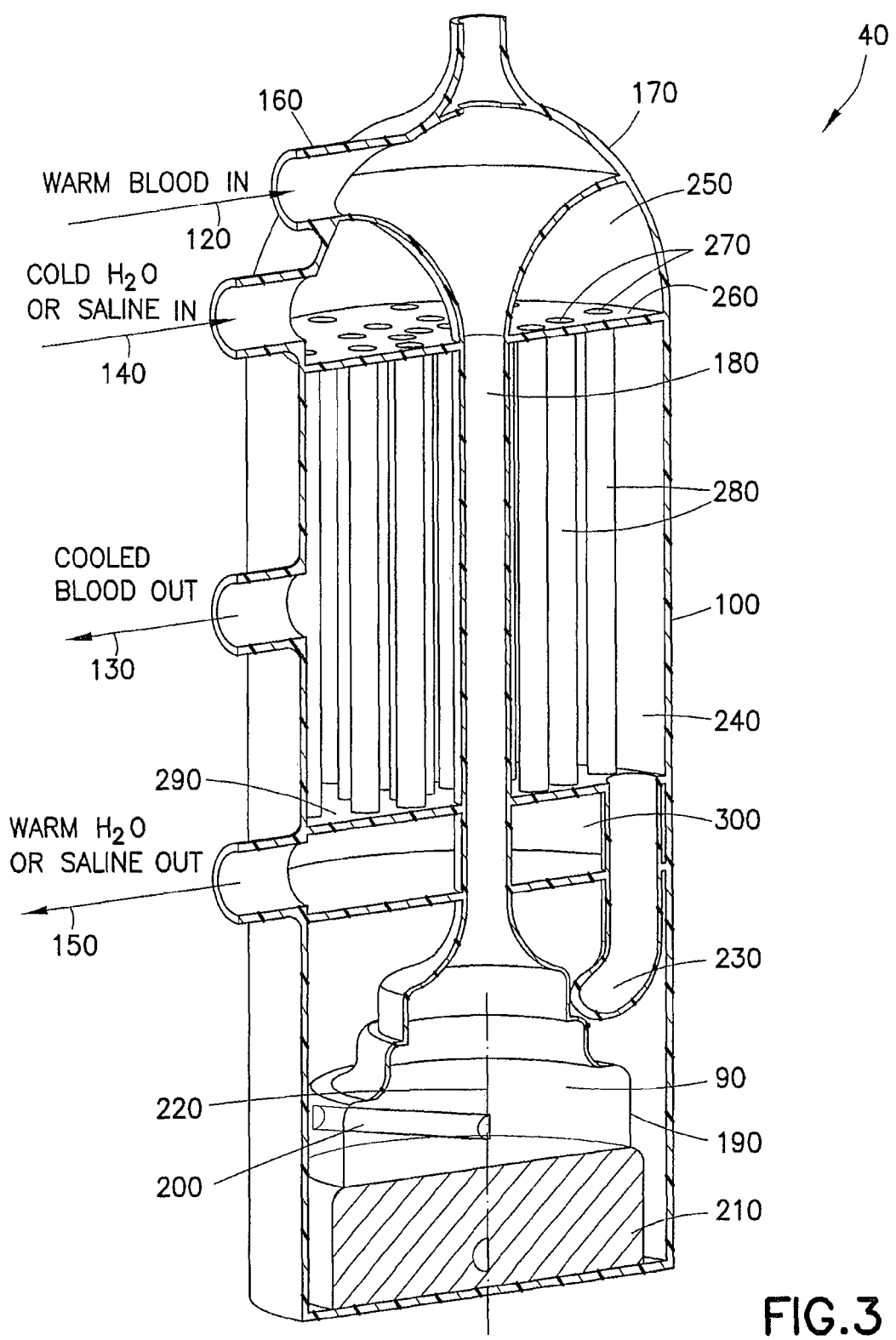
FIG. 3 is a cross-sectional view of the combined pump/heat shown in FIG. 2.

Referring to FIG. 3, one embodiment of the combined pump/heat exchanger 40 is shown. Venous blood is received inside a first chamber 170 after passing through the blood inlet 120. The chamber 170 is in direct fluid communication with the pump 90 via a blood conduit 180 extending substantially along the longitudinal centerline of the housing 110. As previously noted, the pump 90 desirably has the construction of a conventional blood pump. In one embodiment, the pump 90 includes a pump housing 190 in direct fluid communication with the blood conduit 180. The pump housing 190 includes an impeller 200 driven by an electromagnetic drive device 210. It will be apparent that several other embodiments of the pump 90 may be utilized with the pump/heat exchanger device 40 in accordance with this disclosure, including a roller pump. Blood is received into the pump housing 190 (or tubing, if pump 90 is a roller pump) from the blood conduit 180 parallel to the spinning axis 220 of impeller 200. Blood is circulated inside the pump housing 190 and expelled through an outlet 230 into a second chamber 240. The second chamber 240 is contained directly inside the heat exchanger 100 such that heat exchange between blood and the heat exchanger 100 takes place directly inside second chamber 240. After passing through the heat exchanger 100, cooled or heated blood is returned to the patient's body through the blood outlet 130.

With continuing reference to FIG. 3, the heat exchange fluid, such as water or saline solution, enters the heat exchanger 100 through the fluid inlet 140 into the first cavity 250. The first cavity 250 surrounds the first chamber 170 in the upper part of the housing 110. A bottom part of the first cavity 250 includes a first perforated plate 260 having a plurality of fluid openings 270 in direct fluid communication with a plurality of heat exchange tubes 280. The perforated plate 260 separates the first cavity 250 of the heat exchanger 100 from the second chamber 240. The heat exchange tubes 280 extend through the longitudinal length of housing 110 between the first perforated plate 260 located at a top portion of housing 110 and a second perforated plate 290 located at a bottom portion of housing 110. The heat exchange tubes 280 connect to a second cavity 300 provided below the second perforated plate 290 and provide direct fluid communication between the first cavity 250 and second cavity 300. Heat exchange fluid flows from the first cavity 250 to second cavity 300 through the plurality of heat exchange tubes 280. Fluid outlet 150 is in fluid communication with second cavity 280 to expel the heat exchange fluid once it passes through heat exchanger 100.

Components of the combined pump/heat exchanger device 40 are desirably manufactured from a material having thermal characteristics which facilitate heat transfer. For example, the housing 110 and internal components of the pump/heat exchanger device 40 may be manufactured from a metallic or polymeric material having high thermal conductivity. In some embodiments, the pump/heat exchanger device 40 is made from a glass, acrylic, or aluminum materials. Heat can be added or removed from blood flowing through the pump/heat exchanger device 40 depending on the temperature of heat transfer fluid as well as the flow rate through the pump 90. For example, blood can be cooled by circulating a heat exchange fluid through heat exchanger 100 that is cooler than the blood entering the pump/heat exchanger device 40. The temperature of the blood can be lowered further by reducing the flow rate of pump 90 such that blood spends more time inside the heat exchanger 100 when heat exchange fluid has a lower temperature than the blood. Alternatively, blood can be heated by circulating a heat exchange fluid through the heat exchanger 100 that is warmer than the blood entering the pump/heat exchanger. The temperature of the blood can be raised further by reducing the flow rate of the pump 90 such that blood spends more time inside the heat exchanger 100 when heat exchange fluid has a higher temperature than the blood.

Figure 4:
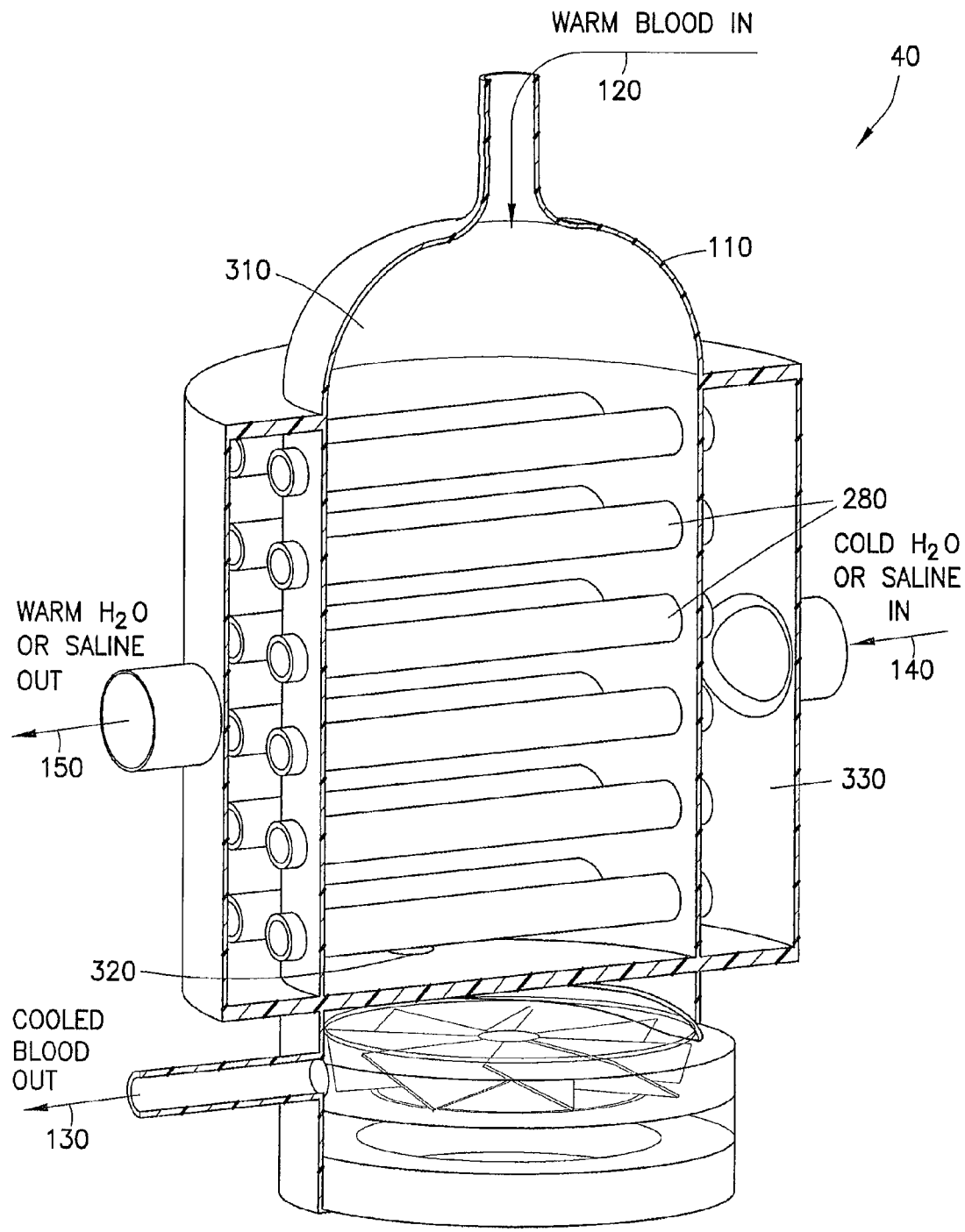
FIG. 4 is a cross-sectional view of the combined pump/heat exchanger according to another embodiment.

With reference to FIG. 4, a second embodiment of the pump/heat exchanger device 40 is shown. In this embodiment, the heat exchange tubes 280 are oriented in a horizontal direction which is perpendicular to the longitudinal axis of the pump/heat exchanger device 40. Venous blood enters the pump/heat exchanger device 40 through the blood inlet 120. Blood is then received inside a blood chamber 310 in direct fluid communication with a blood inlet 320 on the pump 90. After passing through the blood chamber 310, blood is received inside the pump housing 190 parallel to the spinning axis 220 of the impeller 200. Blood is circulated inside the pump housing 190 and expelled through the blood outlet 130.

With continuing reference to FIG. 4, a heat exchanger cavity 330 is located concentric to chamber 310. A plurality of heat exchange tubes 280 extend through the chamber 310 between opposing ends of the heat exchanger cavity 330. Heat exchange fluid is received inside the heat exchanger cavity 330. Heat exchange fluid passes through the plurality of heat exchange tubes 280 and also flows inside the heat exchanger cavity 330 around the chamber 310. The fluid is expelled from the heat exchanger 100 through the fluid outlet 140. The heat exchangers 100 shown in FIGS. 3-4 have the form of a tube-in-tube heat exchanger, where fluid to be cooled or heated flows through a separate conduit from the cooling or heating fluid.

Figure 5:
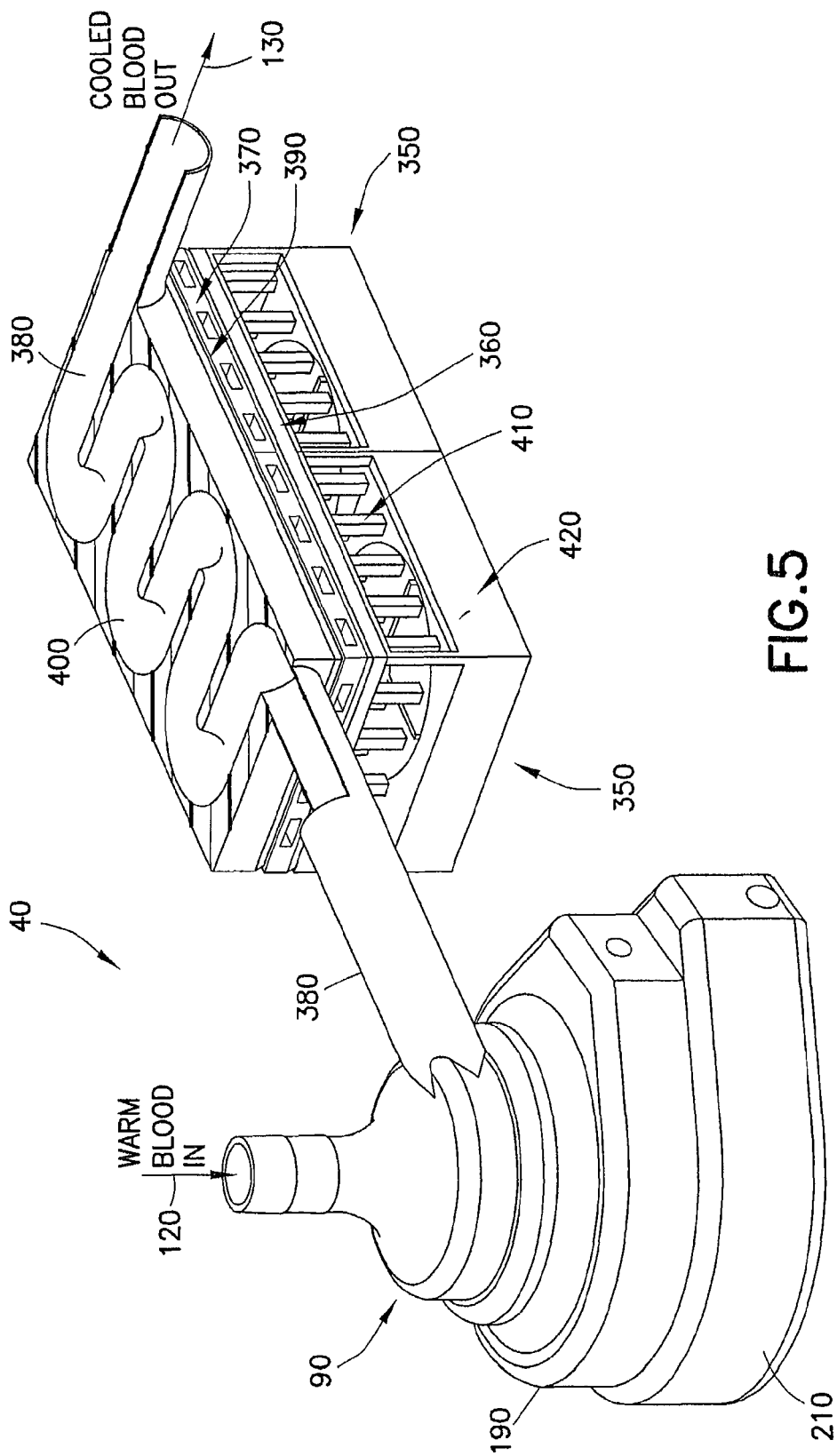
FIG. 5 is a partial cross-sectional view of the pump and the heat exchanger according to a further embodiment.

In an another embodiment shown in FIG. 5, the heat exchanger 100 may utilize a thermoelectric device 350 to add or remove heat from the patient's blood. A thermoelectric device 350 may be a Peltier cell 360 having one or more thermoelectric modules 370 in direct thermal contact with a blood conduit 380. The Peltier cell 360 operates on a Peltier effect principle, whereby a temperature differential is created in different portions of the Peltier cell 360 by applying voltage to semiconductor materials of the thermoelectric modules 370 contained between ceramic substrates 390. Thermal insulation (not shown) may be provided around the heat exchanger 100 to minimize thermal loss and maximize heat transfer efficiency.

As shown in FIG. 5, blood is passed through the pump 90 and is received inside a blood conduit 380 through the blood inlet 120. The blood conduit 380 desirably has a channel 400 defining a tortuous path to increase the amount of time blood spends inside the blood conduit 380. Blood is expelled through the blood outlet 130 located opposite the blood inlet 120. Preferably, the blood conduit 380 is made from a material having high thermal conductivity, such as aluminum, in order to ensure efficient transfer of heat from the blood conduit 380 and Peltier cell 360. The Peltier cell 360 may further include a heat sink 410 for dissipating heat from thermoelectric device 350. A fan 420 is provided to increase the efficiency of heat removal from the heat sink 410. More than one Peltier cell 360 may be provided. The controller 70 desirably controls the operation of the thermoelectric device 350 and the fan 420.

With the basic structure of the extracorporeal blood cooling and heating circuit 10 according to several embodiments now described, a method for rapidly cooling or heating the body temperature will now be generally described. Such a method for rapidly cooling or heating the body temperature of a patient may begin by inserting an intravenous catheter 20 into a patient 30 to withdraw blood into the extracorporeal blood cooling or heating circuit 10. Next step, the controller 70 may be activated to regulate the operation of the pump/heat exchanger device 40, one or more sensors 50, and one or more modules 60 to control the temperature, pressure, and flow rate of blood flowing through the circuit 10. Prior to activating the controller 70, the user may be prompted to initialize and configure the system via an interface 80. Venous blood from the patient 30 is withdrawn into the combined pump/heat exchanger device 40 to be cooled or heated to a desired temperature. Blood is cooled or heated inside the heat exchanger 100 depending on whether the heat exchange fluid that flows through the heat exchanger 100 is cooler or warmer than the blood entering the pump/heat exchanger device 40. Optionally, the blood may be passed through one or more modules 60 to further process the blood. For example, one or more modules 60 may be a blood oxygenating module, a hemodialysis module, etc. After passing through the circuit 10, the blood is returned to the patient 30 in a cooler or warmer state compared to the blood withdrawn from the patient's body.

While embodiments of an apparatus and method for rapidly cooling or heating the body temperature of a patient are shown in the accompanying figures and described in the foregoing in detail, other embodiments will be clear to, and readily made by those skilled in the art, without departing from the scope and spirit of the invention. For example, while the present disclosure generally discusses a centrifugal-type pump 90 and tube-in-tube heat exchanger 100, it is contemplated that various other embodiments of pump 90 and heat exchanger 100 may be equally applicable to the present apparatus and method. The scope of the invention will be measured by the appended claims and their equivalents.

The invention claimed is:

1. An apparatus for rapidly cooling or heating the body temperature of a patient, the apparatus comprising:
   a housing having at least one blood inlet and at least one blood outlet;
   a pump portion contained within the housing for extracting blood from a patient's body through the blood inlet and infusing blood to the patient's body through the blood outlet, the pump portion defining a blood circuit inside the housing between the blood inlet and the blood outlet; and
   a heat exchanger portion contained within the housing for selectively heating or cooling the blood,
   wherein the blood circuit comprises a first chamber with a conically curved bottom wall for receiving the blood from the blood inlet, the bottom wall of the first chamber being in thermal contact with the heat exchanger portion;
   a blood conduit for delivering the blood from the first chamber into a pump, the blood conduit extending through the heat exchanger portion and in thermal contact with the heat exchanger portion; and
   a second chamber for receiving the blood from the pump, the second chamber being within the heat exchanger portion and in thermal contact with the heat exchanger portion.

2. The apparatus according to claim 1, wherein the heat exchanger portion is fluidly connected with at least one fluid inlet to receive a heat exchange fluid and at least one fluid outlet to expel the heat exchange fluid, the fluid inlet and the fluid outlet defining a fluid circuit therebetween.

3. The apparatus according to claim 1, wherein the heat exchanger portion includes a Peltier device having one or more thermoelectric modules in thermal contact with a blood conduit.

4. The apparatus according to claim 2, wherein the blood circuit and the fluid circuit are in fluid isolation from each other inside the housing.

5. The apparatus according to claim 2, wherein the heat exchanger portion further comprises a plurality of heat exchange tubes operative for flowing the heat exchange fluid therethrough, the plurality of heat exchange tubes being in thermal contact with the blood circuit.

6. The apparatus according to claim 2, wherein the apparatus is made from a material having high thermal conductivity to facilitate heat transfer between the blood inside the blood circuit and the heat exchange fluid inside the fluid circuit.

7. An extracorporeal blood cooling or heating circuit comprising:
- a catheter for withdrawing blood from a patient into the extracorporeal blood cooling or heating circuit and infusing blood into the patient from the extracorporeal blood cooling or heating circuit;
- a combined pump/heat exchanger device for selectively cooling or heating the blood;
- one or more sensors operative for measuring blood temperature, pressure, flow, or oxygenation; and
- a controller operatively connected to the combined pump/heat exchanger and one or more sensors for controlling the operation of extracorporeal blood cooling or heating circuit and selectively cooling or heating the blood, wherein the combined pump/heat exchanger device comprises:
  - a housing having at least one blood inlet and at least one blood outlet;
  - a pump portion contained within the housing for extracting blood from the patient through the blood inlet and infusing blood to the patient through the blood outlet, the pump portion defining a blood circuit inside the housing between the blood inlet and the blood outlet; and
  - a heat exchanger portion contained within the housing for selectively heating or cooling the blood,
  - wherein the blood circuit comprises:
    - a first chamber with a conically curved bottom wall for receiving the blood from the blood inlet, the bottom wall of the first chamber being in thermal contact with the heat exchanger portion;
    - a blood conduit for delivering the blood from the first chamber into a pump, the blood conduit extending through the heat exchanger portion and in thermal contact with the heat exchanger portion; and
    - a second chamber for receiving the blood from the pump, the second chamber being within the heat exchanger portion and in thermal contact with the heat exchanger portion.

8. The extracorporeal blood cooling or heating circuit according to claim 7, further comprising one or more modules operative for treating the blood.

9. The extracorporeal blood cooling or heating circuit according to claim 8, wherein the one or more modules is a blood oxygenation device or a hemodialysis device.

10. The extracorporeal blood cooling or heating circuit according to claim 7, wherein the heat exchanger portion is fluidly connected with at least one fluid inlet to receive a heat exchange fluid and at least one fluid outlet to expel the heat exchange fluid, the fluid inlet and the fluid outlet defining a fluid circuit therebetween.

11. The extracorporeal blood cooling or heating circuit according to claim 7, wherein the heat exchanger portion includes a Peltier device having one or more thermoelectric modules in thermal contact with a blood conduit.

12. The extracorporeal blood cooling or heating circuit according to claim 7, wherein the blood circuit and the fluid circuit are in fluid isolation from each other inside the housing.

13. The extracorporeal blood cooling or heating circuit according to claim 7, wherein the heat exchanger portion further comprises a plurality of heat exchange tubes operative for flowing the heat exchange fluid therethrough, the plurality of heat exchange tubes being in thermal contact with the blood circuit.

14. The extracorporeal blood cooling or heating circuit according to claim 7, wherein the apparatus is made from a material having high thermal conductivity to facilitate heat transfer between the blood inside the blood circuit and the heat exchange fluid inside the fluid circuit.

15. A method for rapidly cooling or heating the body temperature of a patient, the method comprising the steps of:
- withdrawing blood from a patient into an extracorporeal circuit having a combined pump/heat exchanger having a pump portion and a heat exchanger portion;
- selectively cooling or heating the blood within the heat exchanger portion to a desired temperature; and
- returning the blood to the patient, wherein the combined pump/heat exchanger comprises:
  - a housing having at least one blood inlet and at least one blood outlet;
  - the pump portion contained within the housing for extracting blood from the patient through the blood inlet and infusing blood to the patient through the blood outlet, the pump portion defining a blood circuit inside the housing between the blood inlet and the blood outlet; and
  - the heat exchanger portion contained within the housing for selectively heating or cooling the blood,
  - wherein the blood circuit comprises:
    - a first chamber with a conically curved bottom wall for receiving the blood from the blood inlet, the bottom wall of the first chamber being in thermal contact with the heat exchanger portion;
    - a blood conduit for delivering the blood from the first chamber into a pump, the blood conduit extending through the heat exchanger portion and in thermal contact with the heat exchanger portion; and
    - a second chamber for receiving the blood from the pump, the second chamber being within the heat exchanger portion and in thermal contact with the heat exchanger portion.

16. The method of claim 15, wherein the heat exchanger portion is fluidly connected with at least one fluid inlet to receive a heat exchange fluid and at least one fluid outlet to expel the heat exchange fluid, the fluid inlet and the fluid outlet defining a fluid circuit therebetween.

* * * * *